(12) United States Patent
Hanes et al.

(10) Patent No.: US 10,307,372 B2
(45) Date of Patent: Jun. 4, 2019

(54) RAPID DIFFUSION OF LARGE POLYMERIC NANOPARTICLES IN THE MAMMALIAN BRAIN

(75) Inventors: Justin Hanes, Baltimore, MD (US); Graeme F. Woodworth, Baltimore, MD (US); Elizabeth A. Nance, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 804 days.

(21) Appl. No.: 13/821,320

(22) PCT Filed: Sep. 12, 2011

(86) PCT No.: PCT/US2011/051195
§ 371 (c)(1),
(2), (4) Date: Mar. 7, 2013

(87) PCT Pub. No.: WO2012/039979
PCT Pub. Date: Mar. 29, 2012

(65) Prior Publication Data
US 2013/0183244 A1 Jul. 18, 2013

Related U.S. Application Data

(60) Provisional application No. 61/381,754, filed on Sep. 10, 2010.

(51) Int. Cl.
*A61K 9/00* (2006.01)
*A61K 9/51* (2006.01)
*A61K 49/00* (2006.01)

(52) U.S. Cl.
CPC .......... *A61K 9/0085* (2013.01); *A61K 9/5138* (2013.01); *A61K 49/0065* (2013.01); *A61K 49/0093* (2013.01)

(58) Field of Classification Search
CPC .............. A61K 9/0085; A61K 9/5138; A61K 49/0065; A61K 49/0093
See application file for complete search history.

(56) References Cited

U.S. PATENT DOCUMENTS

| | | | |
|---|---|---|---|
| 4,997,652 A | 3/1991 | Wong | |
| 5,540,930 A | 7/1996 | Guy | |
| 5,567,435 A | 10/1996 | Hubbell | |
| 5,576,311 A | 11/1996 | Guy | |
| 5,578,325 A | 11/1996 | Domb | |
| 5,696,298 A | 12/1997 | Emanuele | |
| 5,710,135 A | 1/1998 | Leenders | |
| 5,869,130 A | 2/1999 | Ferrier | |
| 5,932,462 A | 8/1999 | Harris | |
| 6,007,845 A | 12/1999 | Domb | |
| 6,117,454 A * | 9/2000 | Kreuter | A61K 9/5138 424/489 |
| 6,270,806 B1 | 8/2001 | Liversidge | |
| 6,287,588 B1 | 9/2001 | Shih | |
| 6,413,539 B1 | 7/2002 | Shalaby | |
| 6,432,381 B2 | 8/2002 | Liversidge | |
| 6,495,164 B1 | 12/2002 | Ramstack | |
| 6,509,323 B1 | 1/2003 | Davis | |
| 6,589,549 B2 | 7/2003 | Shih | |
| 6,706,289 B2 | 3/2004 | Lewis | |
| 8,354,476 B2 | 1/2013 | Hanes | |
| 8,409,607 B2 | 4/2013 | Hughes | |
| 8,465,778 B2 | 6/2013 | Hughes | |
| 8,481,069 B2 | 7/2013 | Hughes | |
| 8,512,738 B2 | 8/2013 | Edelman | |
| 8,628,801 B2 | 1/2014 | Garreta | |
| 8,632,809 B2 | 1/2014 | Asgharian | |
| 8,663,674 B2 | 3/2014 | Wen | |
| 8,889,193 B2 * | 11/2014 | McDonnell | A61K 9/0051 424/490 |
| 8,911,768 B2 | 12/2014 | Whitcup | |
| 8,957,034 B2 * | 2/2015 | Hanes | A61K 9/0073 514/44 R |
| 8,962,577 B2 | 2/2015 | Hanes | |
| 9,056,057 B2 * | 6/2015 | Popov | A61K 9/5031 |
| 2002/0035264 A1 | 3/2002 | Kararli | |
| 2004/0234611 A1 | 11/2004 | Ahlheim | |
| 2004/0241248 A1 | 12/2004 | Margalit | |
| 2005/0009910 A1 | 1/2005 | Hughes | |

(Continued)

FOREIGN PATENT DOCUMENTS

| | | | | |
|---|---|---|---|---|
| EP | 2070521 | * | 6/2009 | ........... A61K 31/427 |
| WO | 9207866 | | 5/1992 | |

(Continued)

OTHER PUBLICATIONS

Liu et al. (Biologically active core/shell nanoparticles self-assembled from cholesterol-terminated PEG-TAT for drug delivery across the blood-brain barrier, Biomaterials, 2008, vol. 29, pp. 1509-1517).*
Betbeder et al. (Influence of surface charge and inner composition of porous nanoparticles to cross blood-brain barrier in vitro, Int. J. Pharm. 2007, vol. 344, pp. 103-109).*
Xu et al. (Intracellular drug delivery by poly(lactic-co-glycolic acid) nanoparticles, revisited, Molecular Pharmaceutics, 2009, vol. 6, pp. 190-201).*
Barbu et al., The potential for nanoparticle based drug delivery to the brain: overcoming the blood-brain barrier, Expert. Opin. Drug Deliv. 2009, vol. 6, p. 556.*
Bramwell et al. Biodegradable mucoadhesive particulates for nasal and pulmonary antigen and DNA delivery, Advanced Drug Delivery Reviews, 2005, vol. 57, pp. 415, 418.*
Gao et al. (Lectin-conjugated PEG-PLA nanoparticles: preparation and brain delivery after intranasal administration, Biomaterials, 2006, vol. 27, pp. 3482-3490).*

(Continued)

*Primary Examiner* — Alma Pipic
(74) *Attorney, Agent, or Firm* — Pabst Patent Group LLP

(57) ABSTRACT

Non-adhesive particles as large as 110 nm can diffuse rapidly in the brain ECS, if coated with hydrophilic coatings such as PEG coatings and preferably having neutral surface charge. The ability to achieve brain penetration with larger particles will significantly improve drug and gene delivery within the CNS since larger particles offer higher drug payload, improved drug loading efficiency, and significantly longer drug release durations.

20 Claims, 3 Drawing Sheets

(56) References Cited

U.S. PATENT DOCUMENTS

| | | | |
|---|---|---|---|
| 2005/0244503 A1* | 11/2005 | Rabinow | A61K 9/1075 424/489 |
| 2007/0053845 A1 | 3/2007 | Sengupta | |
| 2007/0071756 A1 | 3/2007 | Peyman | |
| 2007/0093461 A1 | 4/2007 | Shafiee | |
| 2007/0141143 A1 | 6/2007 | Smithey | |
| 2007/0149593 A1 | 6/2007 | Ghosh | |
| 2007/0231360 A1 | 10/2007 | Peyman | |
| 2007/0249536 A1 | 10/2007 | Ma | |
| 2008/0086199 A1 | 4/2008 | Dave | |
| 2008/0166411 A1 | 7/2008 | Shah | |
| 2008/0305172 A1 | 12/2008 | Ahlheim | |
| 2009/0203709 A1 | 8/2009 | Steinberg | |
| 2009/0247604 A1 | 10/2009 | Tang | |
| 2010/0015051 A1 | 1/2010 | Labhasetwar | |
| 2010/0215580 A1* | 8/2010 | Hanes | A61K 9/0034 424/9.1 |
| 2010/0227905 A1 | 9/2010 | Kabra | |
| 2012/0028910 A1 | 2/2012 | Combal | |
| 2012/0052041 A1 | 3/2012 | Basu | |
| 2012/0157499 A1 | 6/2012 | Hughes | |
| 2012/0269894 A1 | 10/2012 | Ahlheim | |
| 2013/0071349 A1 | 3/2013 | Robinson | |
| 2013/0122064 A1 | 5/2013 | Ahlheim | |
| 2013/0164343 A1 | 6/2013 | Hanes | |
| 2013/0183244 A1 | 7/2013 | Hanes | |
| 2013/0217657 A1 | 8/2013 | Lindstrom | |
| 2013/0236556 A1 | 9/2013 | Lai | |
| 2013/0272994 A1 | 10/2013 | Fu | |
| 2013/0274217 A1 | 10/2013 | Hanes | |
| 2013/0316001 A1 | 11/2013 | Popov | |
| 2013/0316006 A1 | 11/2013 | Popov | |
| 2013/0316009 A1 | 11/2013 | Popov | |
| 2013/0323313 A1 | 12/2013 | Suk | |
| 2014/0031408 A1 | 1/2014 | Edelman | |
| 2014/0107025 A1 | 4/2014 | Wirostko | |
| 2014/0178475 A1 | 6/2014 | Figueiredo | |
| 2014/0248358 A1 | 9/2014 | Figueiredo | |
| 2014/0249158 A1 | 9/2014 | Figueiredo | |
| 2014/0276482 A1 | 9/2014 | Astafieva | |
| 2014/0294986 A1 | 10/2014 | Liu | |
| 2014/0329913 A1 | 11/2014 | Hanes | |
| 2015/0044270 A1 | 2/2015 | McDonnell | |
| 2015/0086484 A1 | 3/2015 | Hanes | |
| 2015/0125539 A1 | 5/2015 | Popov | |
| 2015/0265542 A1 | 9/2015 | Popov | |
| 2015/0265543 A1 | 9/2015 | Popov | |
| 2015/0297531 A1* | 10/2015 | Ensign | A61K 9/0034 424/497 |

FOREIGN PATENT DOCUMENTS

| | | | |
|---|---|---|---|
| WO | 2004060977 | 7/2004 | |
| WO | 2005055985 | 6/2005 | |
| WO | 2006063249 | 6/2006 | |
| WO | 2007016380 | 2/2007 | |
| WO | 2007084418 | 7/2007 | |
| WO | WO2008030557 | * 3/2008 | A61K 9/127 |
| WO | 2008054544 | 5/2008 | |
| WO | WO2009136763 | * 11/2009 | B82B 3/00 |
| WO | 2010040188 | 4/2010 | |
| WO | 2010132664 | 11/2010 | |
| WO | 2011080148 | 7/2011 | |
| WO | 2013110028 | 7/2013 | |
| WO | 2013138343 | 9/2013 | |
| WO | 2013138346 | 9/2013 | |
| WO | 2013166385 | 11/2013 | |
| WO | 2013166408 | 11/2013 | |
| WO | 2013166436 | 11/2013 | |
| WO | 2013166498 | 11/2013 | |
| WO | 2014047439 | 3/2014 | |

OTHER PUBLICATIONS

Salopek et al. Measurement and application of zeta-potential, Rudarsko-geolosko-naftni zbornik, 1992, vol. 4, pp. 147-151.*

Cattaneo et al., Intranasal delivery of therapeutic proteins for neurological diseases, Expert Opin. Drug Deliv. 2011, vol. 8, p. 1277-1296.*

Deosarkar, et al.., "Polymeric particles conjugated with a ligand to VCAM-1 exhibit selective, avid, and focal adhesion to sites of atherosclerosis", Biotech. Bioeng., 101(2):400-7 (2008).

Dong, et al., "Vascular cell-adhesion molecule-1 plays a central role in heproangiogenic effects of oxidative stress", PNAS, 108(35):14614-9 (2011).

Veronese, et al., "PEG-doxorubicin conjugates: influence of polymer structure on drug release, in vitro cytotoxicity, biodistribution, and antitumor activity", Bioconjig Chem.,16(4):775-84 (2005).

Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).

Allard, "Convection-enhanced delivery of nanocarriers for the treatment of brain tumors", Biomaterials, 30(12):2302-18 (2009).

Arifin, et al., "Role of convective flow in carmustine delivery to a brain tumor" Pharm Res., 26(10):2289-302 (2009).

Bobo, et al., "Convection-enhanced delivery of macromolecules in the brain", PNAS, 91(6):2076-80 (1994).

Bundgaard, et al., "Effects of dihydroergotamine on intracranial pressure, cerebral blood flow, and cerebral metabolism in patients undergoing craniotomy for brain tumor", J Neurosurg Anesthesiol, 13(3):195-201 (2001).

Cragg, "Preservation of extracellular space during fixation of the brain for electron microscopy", Tissue Cell, 12(1):63-72 (1980).

Dawson, et al., "Enhanced viscoelasticity of human cystic fibrotic sputum correlates with increasing microheterogeneity in particle transport", J Biol Chem., 278(50):50393-401(2003).

Holtmaat, et al., "Long-term, high-resolution imaging in the mouse neocortex through a chronic cranial window", Nat Protoc., 4(8):1128-44 (2009).

Kunwar, et al., "Direct intracerebral delivery of cintredekin besudotox (IL 13-PE38QQR) in recurrent malignant glioma: a report by the Cintredekin Besudotox Intraparenchymal Study Group", J Clin Oncol., 25(7):837-44 (2007).

Kunwar, et al., "Phase III randomized trial of CED of IL13-PE38QQR vs Gliadel wafers for recurrent glioblastoma", Neuro Oncol., 12:871-81 (2010).

Langsjo, et al., "Effects of subanesthetic doses of ketamine on regional cerebral blood flow, oxygen consumption, and blood volume in humans", Anesthesiology, 99(3):614-23 (2003).

Nicholson and Tao, "Hindered diffusion of high molecular weight compounds in brain extracellular microenvironment measured with integrative optical imaging", Biophys J 65:2277-90 (1993).

Nimkoff, et al., "The effects of intravenous anesthetics on intracranial pressure and cerebral perfusion pressure in two feline models of brain edema", J Crit Care 12(3):132-6 (1997).

Pappas and Purpura, "Distribution of colloidal particles in extracellular space and synaptic cleft substance of mammalian cerebral cortex", Nature, 210(5043):1391-2 (1966).

Popielarski, et al., "A nanoparticle-based model delivery system to guide the rational design of gene delivery to the liver. 1. Synthesis and characterization", Bioconjug Chem., 16(5):1063-70 (2005).

Rosso, et al., "A new model for prediction of drug distribution in tumor and normal tissues: pharmacokinetics of temozolomide in glioma patients", Cancer Res., 69:120-7 (2009).

Sampson, et al., "Poor drug distribution as a possible explanation for the results of the PRECISE trial", J Neurosurg., 113:301-9 (2010).

Schwedler, et al., "Cerebral blood flow and metabolism following ketamine administration", Can Anaesth Soc J., 29(3):222-6 (1982).

Suh, et al., "PEGylation of nanoparticles improves their cytoplasmic transport", Int J Nanomedicine, 2(4):735-41 (2007).

Suh, et al., "Real-time multiple-particle tracking: applications to drug and gene delivery", Adv Drug Deliv Rev., 57:63-78 (2005).

(56) References Cited

OTHER PUBLICATIONS

Suk, et al., "Quantifying the intracellular transport of viral and nonviral gene vectors in primary neurons", Exp Biol Med., (Maywood) 232(3):461-9 (2007).

Suk, et al., "Gene delivery to differentiated neurotypic cells with RGD and HIV Tat peptide functionalized polymeric nanoparticles", Biomaterials, 27:5143-50 (2006).

Sykova and Nicholson, "Diffusion in brain extracellular space", Physiol Rev., 88(4):1277-340 (2008).

Szulczyk, et al., "The effect of acute rise in intracranial pressure on the sympathetic cardiac, vertebral and phrenic nerve activities", Acta Physiol Pol., 27(1):1-8 (1976).

Thorne and Nicholson, "In vivo diffusion analysis with quantum dots and dextrans predicts the width of brain extracellular space", PNAS, 103(14):5567-72 (2006).

Valentine, et al., "Colloid surface chemistry critically affects multiple particle tracking measurements of biomaterials", Biophys J., 86(6):4004-14 (2004).

Van Harreveld and Trubatch, "Progression of fusion during rapid freezing for electron microscopy", J Microsc., 115(3):243-56 (1979).

Wang, et al., "Addressing the PEG mucoadhesivity paradox to engineer nanoparticies that "slip" through the human mucus barrier", Angew Chem Int Ed Engl., 47(50):9726-9 (2008).

Xiao, et al., "Diffusion of flexible random-coil dextran polymers measured in anisotropic brain extracellular space by integrative optical imaging", Biophys J., 95:1382-92 (2008).

Ludwig, "The use of mucosadhesive polymers in ocular drug delivery", Adv Drug Deliv Rev., 57:1595-1639 (2005).

Memon, et al., "Optimization of formulation parameters on ocular loteprednol etabonate nanosuspension by media milling method", Int J Pharmacrut. Biol. Arch., 4:46-51 (2012).

Sahib, et al., "Solubilization of beclomethasone dipropionate in sterically stabilized phospholipid nanomicelies (SSMs):physicochemical and in vitro evaluations", Drug Des Dev Ther., 6:29-42 (2012).

Yang, et al., "Production of virus-mimetic mucus-penetrating particles for drug and gne delivery in mucosal tissues", Annual Meeting of AICHE Science and Engineering Forum, Nov. 16-21, Abstract 705B (2008).

Mastorakos, et al., Highly PEGylated DNA nanoparticles provide uniform and widespread gene transfer in the brain, Adv Health Mater., 4(7):1023-33 (2015).

Mead, et al., "Targeted gene transfer to the brain via the delivery of brain-penetrating DNA nanoparticles with focused ultrasound", J Control Release, 223:109-117 (2016).

Nance, et al., "A dense poly(ethylene glycol) coating improves penetration of large polymeric nanoparticles within brain tissue",, Sci Transl Med.,4(140):149ra119) (2012).

* cited by examiner

US 10,307,372 B2

RAPID DIFFUSION OF LARGE POLYMERIC NANOPARTICLES IN THE MAMMALIAN BRAIN

CROSS-REFERENCE TO RELATED APPLICATIONS

This application claims priority under 35 U.S.C. 371 to PCT/US2011/051195 filed Sep. 12, 2011, entitled "Rapid Diffusion of Large Polymeric Nanoparticles in the Mammalian Brain", by Justin Hanes, Graeme F. Woodworth, and Elizabeth A. Nance, which claims benefit of and priority to U.S. Provisional Patent Application No. 61/381,754 filed on Sep. 10, 2010, all of which are herein incorporated in their entirety by reference.

FIELD OF THE INVENTION

This invention is generally in the field of drug delivery, and in particular, a method of delivering drugs to the brain using coated particles to penetrate brain tissue.

BACKGROUND OF THE INVENTION

While the blood brain barrier has long been considered the crucial interface for therapeutic efficacy within the CNS, more recently poor distribution of agents within the brain itself has emerged as a major delivery challenge. See Arifin, et al. *Pharm Res* 26, 2289 (2009), Bobo et al., *Proc Natl Acad Sci USA* 91, 2076 (1994), Kunwar et al., *Neuro Oncol* 12, 871 (2010), Kunwar et al., *J Clin Oncol* 25, 837 (2007), Rosso et al., *Cancer Res* 69, 120 (2009), and Sampson et al., *J Neurosurg* 113, 301 (2010).

The extracellular space (ECS) in the brain represents the major pathway for movement of many signaling molecules and metabolites as well as therapeutic and diagnostic substances. This space between cells comprises 15-20% of the total brain volume, contains charged and hydrophobic regions, and shifts with changes in cerebral metabolic activity, blood flow, and spinal fluid dynamics. Importantly, the ECS may be more complex in certain pathogenic states, such as intrinsic invasive brain tumors.

It was previously believed that only neutral or negatively charged substances ≤40 nm in diameter could passively diffuse through the brain ECS. See Xiao, et al. *Biophys J* 95, 1382 (2008); Thorne, et al *Proc Natl Acad Sci USA* 103, 5567 (2006). For substances with few adhesive interactions, this size is large enough to allow diffusion of nanoparticles, but too small to allow efficient penetration of many particulate drug delivery systems and viruses carrying therapeutic genes. Thus, the brain ECS poses a formidable barrier to therapy with some of the most advanced new treatment modalities.

Passive movements of neurotransmitters, cytokines, chemokines, nutrients, and metabolites are critical to brain function. This movement is regulated in part by the multi-faceted extracellular environment in the brain. The diffusion of various substances in the brain extracellular space (ECS) has been studied extensively. A key factor and limitation to diffusion is the 'mesh spacing' or 'pore size' within the brain ECS.

Understanding the microstructure and mesh spacing of the brain microenvironment has important implications for development of therapeutic and diagnostic nanoparticles, as movement through this space is critical for effective distribution and/or targeting. Numerous studies have estimated the brain ECS mesh size, with early efforts focused on electron microscopy to directly measure structures and spaces in fixed or frozen tissues (Cragg B (1980) *Tissue Cell* 12(1):63-72; Pappas G D & Purpura D P (1966) *Nature* 210(5043):1391-1392). This data has been criticized for poor preservation of the tissue architecture and therefore, artifactual results (Cragg 1980; Van Harreveld A & Trubatch J (1979) *J Microsc* 115(3):243-256). More recently, confocal and multi-photon microscopy have been used to measure the movement of fluorescent molecules or particles in brain slices as well as the cortical surface in vivo. From the fluorescent spread data, the apparent diffusion coefficients for the fluorescent probes were calculated and, from this, ECS mesh spacing was estimated.

While these models reduce the problems inherent to EM measurements, the modeling calculations based on gross particle spread and Fick's Law cannot resolve or analyze trajectories of individual particles and, therefore, are unable to assess micro-rheology, anisotropy, and small-scale Brownian motion. In addition, these methods do not account for bulk flow phenomenon or convective forces introduced by the injection process.

Measurement of the brain ECS pore size has proven to be challenging. Artifacts introduced with tissue preservation and processing as well as the structural heterogeneity of the tissue including anisotropic, electro-statically charged regions and dead-space micro-domains, make many measurements unreliable. Importantly, this space in the living brain is not a static medium. There is continuous cerebral spinal fluid (CSF) bulk flow as well as relative volume fraction and tortuosity changes resulting from cell volume changes in response to varying levels of metabolic activity and anesthetic drugs Sykova et al. *Physiol Rev* 88(4):1277-1340 (2008), Thorne 2006; Bundgaard et al. *J Neurosurg Anesthesiol* 13(3):195-201 (2001); Holtmaat et al. *Nat Protoc* 4(8):1128-1144 (2009); Langsjo et al. *Anesthesiology* 99(3):614-623 (2003); Nimkoff et al. *J Crit Care* 12(3):132-136 (1997); Schwedler et al. *Can Anaesth Soc J* 29(3):222-226 (1982); Szulczyk et al. *Acta Physiol Pol* 27(1):1-8 (1976). Current data suggests the average mesh spacing to be ≤40 nm, based on the spread of fluorescent probes in the living rat brain (Thorne 2006 and Xiao 2008). While this represents a significant improvement from the earlier EM-based methods, these calculations did not account for convective and bulk flow forces, anesthetic-induced changes, tissue anisotropy, or potential adhesive interactions with the experimental probes.

Moreover, it was believed that a negative or neutral surface charge would enable less interaction and improved diffusion in the brain (Sykova E & Nicholson C (2008) *Physiol Rev* 88(4):1277-1340; Allard (2009) *Biomaterials* 30(12):2302-2318). In the 2006 study by Thorne and Nicholson, *Proc Natl Acad Sci USA* 103(14):5567-5572, PEG-coated quantum dots approximately 35 nm in size with net negative surface charge were used. It is possible that the upper pore size limit set by hindered diffusion of these larger particles was due to hydrophobic and/or electrostatic interactions (surface chemistry) and not steric (size) considerations.

It is therefore an object of the present invention to provide detailed analysis and characterization of the brain tissue, especially of the ECS pore size, as well as the role of surface charge and hydrophobicity/hydrophilicity on and particle penetration in, and drug delivery to, the brain.

It is a further object of the present invention to use this information to provide the particle characteristics that enable maximum drug loading and release times for delivery of therapeutic, prophylactic and diagnostic agents to the brain, while optimizing or maximizing penetration.

SUMMARY OF THE INVENTION

Dosage formulations containing nanoparticles, particularly nanoparticles which exhibit increased rates of diffusion through the brain, and methods of making and using thereof, are described herein. In a particular embodiment, the nanoparticles have encapsulated therein and/or associated with the surface of the particles, one or more therapeutic, prophylactic, and/or diagnostic agents.

In one embodiment, the particles have an average size (e.g., diameter) from about 20 to about 230 nm, or between 20 and 230 nm, preferably from about 60 to about 110 nm or between about 60 and about 110 nm. In another embodiment, the particles have an average size (e.g., diameter) from about 110 nm to about 200 nm, such as 110, 120, 130, 140, 150, 160, 170, 180, or 190 nm.

In a particular embodiment, the particles are coated with one or more materials which facilitate or enhance diffusion of the particles, particularly through the brain. The coating material can be a surfactant or a hydrophilic material, such as a hydrophilic polymer. In one embodiment, the material is polyethylene glycol (PEG) or a PEG-containing polymer, such as a PEG-containing block copolymer. In one embodiment, the particles are densely coated with the coating material. In a particular embodiment, the density of the coating is such that the surface of the particle is near-neutral as measured by the zeta potential of the surface and/or the particles exhibit significantly reduced adhesion to tissue compared to uncoated particles. In another embodiment, the density of the coating is such that the particle penetrates brain tissue at a rate significantly faster than an uncoated particle. The density of the coating can be expressed as units per $nm^2$ or as the ratio of the mass of the coating to the mass of the particle or as the weight percent of the coating.

The nanoparticles can be combined with one or more pharmaceutically acceptable excipients and/or carriers to form pharmaceutical formulations. The formulations can be administered directly or indirectly to the brain using methods of administration known in the art.

In a study utilizing an ex vivo living brain slice model coupled with real-time multiple particle tracking to study the non-convective movement of densely-coated nanoparticle probes in the brain extracellular space, the results show that non-adhesive particles as large as 110 nm can diffuse rapidly in the brain ECS. In another study, results demonstrate that particles larger than the reported ECS mesh size rapidly penetrate within the brain, if well-coated to minimize adhesive interactions. The human tissue ECS was found to have pores as large as 300 nm, with a high percentage >100 nm. This is significantly larger than previously thought, likely due to adhesion of particles used in prior studies from inadequate surface shielding. Studies on the movements of nanoparticles of various diameters in human brain tissue freshly obtained from the operating room were conducted. Nanoparticles used included standard polystyrene beads with negatively-charged carboxylate surface chemistry, and the same particles engineered with exceptionally dense coatings of low molecular weight polyethylene glycol (PEG) to provide a neutrally-charged, bio-inert surface. Nanoparticles as large as 110 nm in diameter penetrated within the human brain, but only if they were densely coated with low molecular weight PEG.

The ability to achieve brain penetration with larger particles will significantly improve drug and gene delivery within the CNS since larger particles offer higher drug payload, improved drug loading efficiency, and significantly longer drug release durations.

DETAILED DESCRIPTION OF THE INVENTION

Figures 1A, 1B, 1C:
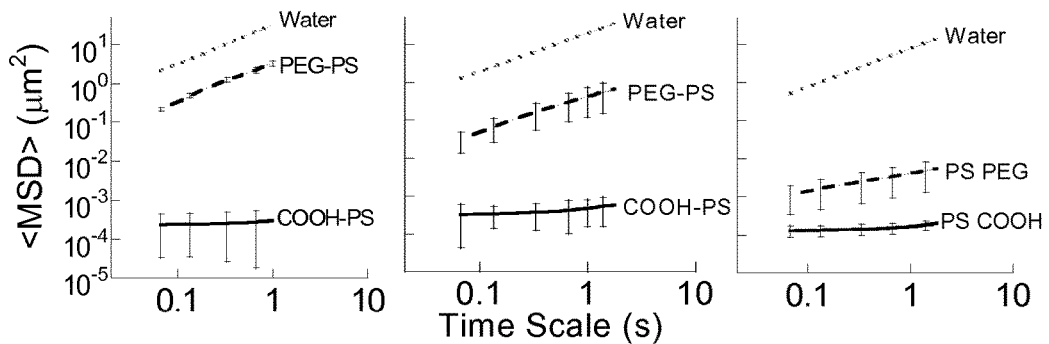
FIGS. 1A-1C are graphs showing ensemble-averaged geometric mean square displacements (<MSD>) as a function of time scale for 40 nm (FIG. 1A), 100 nm (FIG. 1B), and 200 nm (FIG. 1C) PEG-PS compared to COOH—PS. Data represent the ensemble average of at least three independent experiments, with n≥100 particles for each experiment and average n=127, 396, and 352 for 40 nm, 100 nm, and 200 nm PEG-PS and COOH—PS, respectively. For each experiment, the transport rates of all three particle sizes with two different surface properties were measured in the same brain tissue. * indicates a statistically significant difference at p<0.05 compared to COOH modified particles of the same size. The dotted lines indicate theoretical MSD values for the same size PS particles in pure water.

Diffusion in the ECS is a major barrier in the brain for therapeutic and diagnostic molecules as well as delivery vehicles. Nanoparticles larger than the reported mesh-pore size range (40 nm) in brain ECS were thought to be too large to undergo rapid transport. Multiple particle tracking techniques were used to (i) determine the effect of size and surface chemistry on particle transport in the brain microenvironment, and (ii) estimate the ECS average pore size and pore size range in the mammalian brain.

In a study utilizing an ex vivo living brain slice model coupled with real-time multiple particle tracking to study the non-convective movement of densely-coated nanoparticle probes in the brain extracellular space, the results show that non-adhesive particles as large as 110 nm can diffuse rapidly in the brain ECS. In another study, results demonstrate that the brain ECS has a large percentage of pores >100 nm, and particles larger than the reported ECS mesh size rapidly penetrate within the brain, but only if well-coated to minimize adhesive interactions. Both findings have significant implications for particle mediated therapies and diagnosis in the brain.

It was previously believed that only neutral or negatively charged substances ≤40 nm in diameter could passively diffuse through the ECS of the brain. This size is large enough to allow diffusion of signaling molecules, nutrients and metabolic waste products, but too small to allow efficient penetration of most particulate drug delivery systems and viruses carrying therapeutic genes. The movements of nanoparticles of various diameters in human brain tissue freshly obtained from the operating room were measured. Nanoparticles used included standard polystyrene beads with negatively-charged carboxylate surface chemistry, and the same particles engineered with exceptionally dense coatings of a coating material, such as low molecular weight polyethylene glycol (PEG), to provide a neutrally-charged or near-neutrally charged, bio-inert surface. Particle transport rates were analyzed using real-time high resolution multiple particle tracking. To confirm these ex vivo human brain findings, in vivo mouse brain imaging was used to directly observe the relative spread of each particle type in the living brain. Nanoparticles as large as 110 nm in diameter penetrated within the human brain, but only if they were densely coated with low molecular weight PEG. The human tissue ECS was found to have pores as large as 300 nm, with a high percentage >100 nm. This is significantly larger than previously thought, likely due to particles used in previous studies adhering from inadequate surface shielding. The ability to achieve brain penetration with larger particles will significantly improve drug and gene delivery within the CNS since larger particles offer higher drug payload, improved drug loading efficiency, and significantly longer drug release durations.

I. Definitions

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "corresponding particle" or "reference particle" as used herein refers to a particle that is substantially identical to another particle to which it is compared, but typically lacking a surface modification to promote transport differences through the pores in the ECS of the brain. A corresponding particle may be of similar material, density, and size as the particle to which it is compared. In certain embodiments, a corresponding particle is a carboxyl-modified polystyrene (PS) particle, e.g., available from Molecular Probes, Eugene, Oreg. In certain embodiments, a comparable particle is a polystyrene particle that has carboxyl, amine or sulfate aldehyde surface modifications.

The term "DNA" refers to a polymer of deoxynucleotides. Examples of DNA include plasmids, gene therapy vector, and a vector designed to induce RNAi.

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Sustained release" as used herein refers to release of a substance over an extended period of time in contrast to a bolus type administration in which the entire amount of the substance is made biologically available at one time.

The term "microspheres" is art-recognized, and includes substantially spherical colloidal structures, e.g., formed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10% of the median volume diameter.

The term "particle" as used herein refers to any particle formed of, having attached thereon or thereto, or incorporating a therapeutic, diagnostic or prophylactic agent, optionally including one or more polymers, liposomes micelles, or other structural material. A particle may be spherical or nonspherical. A particle may be used, for example, for diagnosing a disease or condition, treating a disease or condition, or preventing a disease or condition.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrasternal injection and infusion.

The term "surfactant" as used herein refers to an agent that lowers the surface tension of a liquid.

The term "therapeutic agent" refers to an agent that can be administered to prevent or treat a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

The term "treating" preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine;

The term "prolonged residence time" as used herein refers to an increase in the time required for an agent to be cleared from a patient's body, or organ or tissue of that patient. In certain embodiments, "prolonged residence time" refers to an agent that is cleared with a half-life that is 10%, 20%, 50% or 75% longer than a standard of comparison such as a comparable agent without a mucus-resistant coating. In certain embodiments, "prolonged residence time" refers to an agent that is cleared with a half-life of 2, 5, 10, 20, 50, 100, 200, 500, 1000, 2000, 5000, or 10000 times longer than a standard of comparison such as a comparable agent without a coating the promotes diffusion through the pores of the ECS of the brain.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of one or more diseases or disorders of the brain, such as reducing tumor size (e.g., tumor volume) or reducing or diminishing one or more symptoms of a neurological disorder, such as memory or learning deficit, tremors or shakes, etc. In still other embodiments, an "effective amount" refers to the amount of a therapeutic agent necessary to repair damaged neurons and/or induce regeneration of neurons.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

II. Compositions

A. Particles

1. Size

The ability of larger particles to diffuse into tissues holds many important implications for nanoparticle-based drug delivery and diagnostic systems. First, large particles have an enormous advantage over smaller particles for delivering drugs or diagnostic agents to tissues. This is not only because theoretical drug payload per particle increases with particle radius to the third power, but also because the ability to encapsulate a wide variety of therapeutics is significantly improved with the greater particle volume. By increasing particle size from 30 nm (expected to be capable of diffusing within ECS) to 100 nm (not previously expected to be capable), one can achieve more than 1000-fold higher drug loading per particle. Another advantage is that it is very difficult to attain slow release kinetics of molecules entrapped in small particles, whereas it is relatively straightforward to do so with larger particles. Taken together, these results show that the increased particle size described here should have significant impact on the ability to use nano-sized carriers for delivery of diagnostic and therapeutic agents in the brain.

In some embodiments, the particles have an average diameter greater than the pores in the extracellular space (ECS) of the brain. As discussed below, the brain ECS was found to have pores as large as 300 nm, with a high percentage having pores larger than 100 nm. In particular embodiments, the particles have an average diameter up 230 nm, preferably from about 40 to about 110 nm, more preferably from about 60 to about 110 nm as measured using dynamic light scattering. In another embodiment, the particles have a diameter from about 110 to about 200 nm, such as about 110, 120, 130, 140, 150, 160, 170, 180, or 190 nm. The ranges above are inclusive of all values between the minimum and maximum values.

In another embodiment, the particles have an average diameter such that a majority of the particles do not become localized within cells or microdomains within tissue compared to larger particles. As shown in the examples, particles having an average particle size of 40 nm showed an even larger difference in diffusion in brain ECS versus water ($D_b/D_w$=76,000) compared to 100 nm and 200 nm COOH— PS particles. It was observed that these particles were more frequently localized within cells or small microdomains in the brain. In particular embodiment, the particles have a diameter greater than 40 nm, particularly greater than 60 nm and preferably less than 250 nm, more preferably less than 230 nm. The particles may have a size less than 60 nm provided the coating(s) resulting in enhanced penetration of a higher percentage of the particles.

2. Core Polymer

Any number of biocompatible polymers can be used to prepare the nanoparticles. In one embodiment, the biocompatible polymer(s) is biodegradable. Exemplary polymers include, but are not limited to, cyclodextrin-containing polymers, in particular cationic cyclodextrin-containing polymers, such as those described in U.S. Pat. No. 6,509,323, poly(caprolactone) (PCL), polyhydroxy acids and copolymers thereof such as poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethanes, polyamino acids such as poly-L-lysine (PLL), poly(valeric acid), and poly-L-glutamic acid, hydroxypropyl methacrylate (HPMA), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), ethylene vinyl acetate polymer (EVA), polyvinyl alcohols (PVA), polyvinyl ethers, polyvinyl esters such as poly(vinyl acetate), polyvinyl halides such as poly(vinyl chloride) (PVC), and polyvinylpyrrolidone, polysiloxanes, polystyrene (PS), celluloses including derivatized celluloses such as alkyl celluloses, hydroxyalkyl celluloses, cellulose ethers, cellulose esters, nitro celluloses, hydroxypropylcellulose, and carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), polydioxanone and its copolymers, polyhydroxyalkanoates, polypropylene fumarate, polyoxymethylene, poloxamers, poly(butyric acid), trimethylene carbonate, polyphosphazenes, and combinations thereof.

The carboxyl termini of carboxylic acid contain polymers, such as lactide- and glycolide-containing polymers, may optionally be capped, e.g., by esterification, and the hydroxyl termini may optionally be capped, e.g. by etherification or esterification.

Copolymers of two or more polymers described above, including block and/or random copolymers, may also be employed to make the polymeric particles.

Copolymers of PEG or derivatives thereof with any of the polymers described above may be used to make the polymeric particles. In certain embodiments, the PEG or derivatives may locate in the interior positions of the copolymer. Alternatively, the PEG or derivatives may locate near or at the terminal positions of the copolymer. In certain embodiments, the microparticles or nanoparticles are formed under conditions that allow regions of PEG to phase separate or otherwise locate to the surface of the particles. The surface-localized PEG regions alone may perform the function of, or include, a surface-altering agent.

Examples of preferred natural polymers include proteins such as albumin, collagen, gelatin and prolamines, for example, zein, and polysaccharides such as alginate.

3. Coatings

The nanoparticles preferably are coated with one or more materials (e.g., surface altering agents) that promote diffusion of the particles through the ECS in the brain by reducing interactions between the particles and brain tissue (e.g., reduce adhesion). Examples of the surface-altering agents include, but are not limited to, anionic proteins (e.g., albumin), surfactants (e.g. polyvinyl alcohol), sugars or sugar derivatives (e.g., cyclodextrin), and polymers. Preferred polymers include heparin, polyethylene glycol ("PEG") and poloxamers (polyethylene oxide block copolymers). The most preferred coating material is PEG.

Certain agents such as cyclodextrin may form inclusion complexes with other molecules and can be used to form attachments to additional moieties and facilitate the functionalization of the particle surface and/or the attached molecules or moieties.

Examples of surfactants include but are not limited to L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil, lecithin, oleic acid, and sorbitan trioleate.

In one embodiment, the particles are coated with polyethylene glycol (PEG). Poly(ethylene glycol) may be employed to reduce adhesion in brain ECS in certain configurations, e.g., wherein the length of PEG chains extending from the surface is controlled (such that long, unbranched chains that interpenetrate into the ECS are reduced or eliminated). For example, linear high MW PEG may be employed in the preparation of particles such that only portions of the linear strands extend from the surface of the particles (e.g., portions equivalent in length to lower MW PEG molecules). Alternatively, branched high MW PEG may be employed. In such embodiments, although the molecular weight of a PEG molecule may be high, the linear length of any individual strand of the molecule that extends from the surface of a particle would correspond to a linear chain of a lower MW PEG molecule.

Representative PEG molecular weights include 300 Da, 600 Da, 1 kDa, 2 kDa, 3 kDa, 4 kDa, 6 kDa, 8 kDa, 10 kDa, 15 kDa, 20 kDa, 30 kDa, 50 kDa, 100 kDa, 200 kDa, 500 kDa, and 1 MDa and all values within the range of 300 Daltons to 1 MDa. In preferred embodiments, the PEG has a molecular weight of about 5,000 Daltons. PEG of any given molecular weight may vary in other characteristics such as length, density, and branching.

The density of the coating can be varied based on a variety of factors including the surface altering material and the composition of the particle. In one embodiment, the density of the surface altering material is at least 0.001, 0.002, 0.005, 0.008, 0.01, 0.02, 0.05, 0.08, 0.1, 0.2, 0.5, 0.8, 1, 2, 5, 8, 10, 15, 20, 25, 40, 50, 60, 75, 80, 90, or 100 units per $nm^2$. The range above is inclusive of all values from 0.001 to 100 units per $nm^2$.

In another embodiment, the amount of the surface-altering moiety is expressed as a percentage of the mass of the particle. In a particular embodiment, the mass of the surface-altering moiety is at least $1/10,000$, $1/7500$, $1/5000$, $1/4000$, $1/3400$, $1/2500$, $1/2000$, $1/1500$, $1/1000$, $1/750$, $1/500$, $1/250$, $1/200$, $1/150$, $1/100$, $1/75$, $1/50$, $1/25$, $1/20$, $1/5$, $1/2$, or $9/10$ of the mass of the particle. The range above is inclusive of all vales from $1/10,000$ to $9/10$. In another embodiment, the weight percent of the surface altering material is at least 80%, 81%, 82%, 83%, 84%, 85%, 86%, 87%, 88%, 89%, 90%, 91%, 92%, 93%, 94%, 95%, or greater. The range above is inclusive of all values from 80% to 95%.

4. Particle Properties

As shown in the examples, the particles diffuse through the pores of the ECS of the brain at a greater rate of diffusivity than a reference particle, such as an uncoated particle, e.g., uncoated polystyrene particle.

The particles described herein may pass through the pores of the ECS of the brain at a rate of diffusivity that is at least 10, 20, 25, 30, 40, 50, 60, 75, 80, 100, 125, 150, 175, 200, 250, 500, 600, 750, 1000, 1500, 2000, 2500, 3000, 4000, 5000, 7500, or 10000- or greater fold higher than a reference particle when measured in vitro. The range above is inclusive of all values from 10 to 10,000.

The transport rates of the particles can be measured using a variety of techniques in the art. In one embodiment, the rate of diffusion is measured by geometric ensemble mean squared displacements (MSD). In a particular embodiment, the particles may diffuse through the pores of the ECS of the brain with an MSD that is at least 5, 20, 30, 50, 60, 75, 80, 100, 125, 150, 200, 250, 500, 600, 750, 1000, 1500, 1750, 2000, 2500, 3000, 4000, 5000, 10000- or greater fold higher than a reference particle. The range above is inclusive of all values from 5 to 10,000.

In other embodiments, the particles diffuse through the pores of the ECS of the brain at a rate approaching the rate of diffusivity at which the particles diffuse through water. In a particular embodiment, the rate of diffusivity is at least $1/10,000$, $1/7500$, $1/5000$, $1/1000$, $1/800$, $1/700$, $1/600$, $1/500$, $1/400$, $1/250$, $1/200$, $1/150$, $1/100$, $1/75$, $1/50$, $1/25$, $1/10$, $1/7$, $1/5$, $1/2$, or 1 times the rate of diffusivity of the particle in water under identical conditions. The range above is inclusive of all values from $1/10,000$ to 1. For example, at a time scale of 1 s, the rates of diffusion of 40 nm, 100 nm, and 200 nm COOH—PS particles (i.e., unmodified or reference particles) were 76,000-fold, 16,000-fold, and 48,000-fold slower in brain tissue than the same particles in water. In contrast, at a time scale of 1 s, PEG-coated particles exhibit 9-fold and 60-fold higher ensemble MSDs in water, respectively, compared with the corresponding COOH—PS particles of the same size.

The heterogeneity in particle transport rates can also be evaluated by examining the distribution of individual particle diffusivities at over a particular time period, e.g., 1 s. For example, in the examples below, the fastest 75% of the 40 nm and 65% of the 100 nm PEG-PS particles exhibited uniformly rapid transport compared to the Fastest 15% of the 200 nm PEG-PS particles. Such fast moving outlier particles are more likely to penetrate brain tissue and reach greater distances from the point of injection The particles can be classified based on their mode of transport: diffusive, hindered, or immobile. The τ-dependent {MSD} is fitted to the equation $\{MSD\}=4D_o\tau^\alpha$, where $D_o$ is the τ-dependent diffusivity and a is the anomalous diffusion exponent that reflects the extent of impediment. An $\alpha=1$ represents unobstructed Brownian diffusion, such as particles in water, where α becomes smaller as obstruction to particle diffusion increases. Hindered particles have an α value closer to 0, where diffusive particles have an α value closer to 1. In the case where particles experience strong impediment due to interactions with components of the brain ECS, particles typically have an MSD below the microscope detection limit (e.g., 10 nm) and are classified as immobile. In one embodiment, at least 15%, 20%, 25%, 30%, 35%, 40%, 45%, 50%, 55%, 60%, 65%, 70%, 75%, 80%, or greater of coated particles of a given average particle size are classified as diffusive. The range of above is inclusive of all values from 15% to 80%.

The presence of the surface-altering agent can affect the zeta-potential of the particle. In one embodiment, the zeta potential of the particles is −100 mV and 10 mV, between −50 mV and 10 mV, between −25 mV and 10 mV, between −20 mV and 5 mV, between −10 mV and 10 mV, between −10 mV and 5 mV, between −5 mV and 5 mV, or between −2 mV and 2 mV. In a preferred embodiment, the surface charge is neutral or near-neutral. The range above is inclusive of all values from −100 mV to 10 mV.

B. Therapeutic, Diagnostic and Prophylactic Agents to be Delivered

The nanoparticles described herein can be used to deliver one or more active agent, particularly one or more active agents to prevent or treat one or more diseases or disorders of the brain. Suitable active agents include therapeutic, diagnostic, and/or prophylactic agents. The agent can be a biomolecule, such as an enzyme, protein, polypeptide, or nucleic acid or a small molecule agent (e.g., molecular weight less than 2000 amu, preferably less than 1500 amu), including organic, inorganic, and organometallic agents. The agent can be encapsulated within the particles, dispersed within the particles, and/or associated with the surface of the particle, either covalently or non-covalently.

Therapeutic agents include chemotherapeutic agents, agents for treatment or alleviation of neurological diseases and disorders, anti-inflammatories, agents for treatment of brain trauma, antiinfectives, and combinations thereof.

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radioopaque. Nanoparticles can further include agents useful for determining the location of administered particles. Agents useful for this purpose include fluorescent tags, radionuclides and contrast agents.

For those embodiments where the one or more therapeutic, prophylactic, and/or diagnostic agents are encapsulated within a polymeric nanoparticle and/or associated with the surface of the nanoparticle, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a nanoparticle and associated with the surface of the particle.

C. Pharmaceutical Excipients for Delivery to the Brain

The particles may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In preferred embodiments, the particles are formulated for parenteral delivery to the brain. Typically the particles will be formulated in sterile saline or buffered solution for injection into the tissues or cells to be treated. The particles can be stored lyophilized in single use vials for rehydration immediately before use. Other means for rehydration and administration are known to those skilled in the art.

Optional pharmaceutically acceptable excipients include, but are not limited to, lubricants, disintegrants, colorants, stabilizers, and surfactants.

Stabilizers are used to inhibit or retard decomposition reactions which include, by way of example, oxidative reactions.

The nanoparticles or nanoconjugates are preferably formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions will be decided by the attending physician within the scope of sound medical judgment. For any nanoparticle or nanoconjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

II. Methods of Manufacture

A. Particles

Nanoparticles can be made using a variety of techniques in the art. The technique to be used can depend on a variety of factors including the polymer used to form the microparticles and the desired size range of the resulting particles. The type of active agent to be incorporated into the particles may also be a factor as some agents are unstable in the presence of organic solvents and/or high temperatures.

Methods for preparing particles include, but are not limited to:

a. Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation.

In this method, the polymer is first melted and then mixed with the solid particles. The mixture is suspended in a non-miscible solvent (like silicon oil), and, with continuous stirring, heated to 5 C above the melting point of the polymer. Once the emulsion is stabilized, it is cooled until the polymer particles solidify. The resulting nanoparticles are washed by decantation with petroleum ether to give a free-flowing powder. The external surfaces of spheres prepared with this technique are usually smooth and dense. This procedure is used to prepare nanoparticles made of polyesters and polyanhydrides. However, this method is limited to polymers with molecular weights between 1,000-50,000.

c. Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

d. Spray-Drying.

In this method, the polymer is dissolved in organic solvent. A known amount of the active drug is suspended (insoluble drugs) or co-dissolved (soluble drugs) in the polymer solution. The solution or the dispersion is then spray-dried.

e. Phase Inversion.

Microspheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposomes).

B. Surface-Altering Coatings

The particles can be coated with the surface-altering agent using a variety of techniques known in the art depending on whether the coating is covalently or non-covalently associated with the particles. The material can be applied non-covalently, for example, by spray drying.

The coating can be covalently attached to the particles by reacting functional groups on the particles with reactive functional groups on the agent to be attached. For example, aminated PEG can be reacted with reactive functional groups on the particles, such as carboxylic acid groups, to covalently attach the agent via an amide bond. In other embodiments, a spacer molecule may be incorporated between the particle surface and the surface-altering agent.

III. Methods of Use

The particle compositions described herein can be used to administer one or more therapeutic, prophylactic, and/or diagnostic agents directly to the brain to treat one or more diseases or disorders of the brain.

A. Disorders or Diseases to be Treated

In general, these encompass any disease requiring treatments or diagnostic approaches wherein the effect of the active agent(s) would be improved by enhanced tissue penetration, cellular or structural targeting, concomitant delivery, and/or sustained-release, particularly in the brain.

Exemplary diseases and disorders of the brain include, but are not limited to, neoplasms (e.g., cancers, tumors, growths); infections (e.g., HIV/AIDS, Tuberculosis); inflammation (e.g., multiple sclerosis, transverse myelitis and other autoimmune processes, cerebral or tissue edema and other reactive processes); acquired or degenerative conditions (Alzheimer's disease, Parkinson's disease, Stroke, Amylotrophic Lateral Sclerosis, Acute and Chronic Traumatic and Pain syndromes); congenital or genetic abnormalities (e.g., Neurofibromatosis, Mucopolysaccaridoses, Tuberous Sclerosis, Von Hippel Lindau); epigenetic conditions, and brain trauma or injury, such as battlefield injuries.

B. Methods of Administration and Dosing

The nanoparticle compositions described herein can be administered using a variety of routes of administration. In some embodiments, the nanoparticle compositions are administered locally to the site/tissue of interest, for example, via direct administration to the brain. Enhanced local delivery can be achieved via convection, electromagnetic, or other forces.

Other modes of administration include intrathecal or intra-ventricular delivery via cerebro-spinal fluid spaces; intra-nasal administration or delivery via the olfactory bulb; and systemic delivery via oral, intravenous, or intra-arterial administration.

Enhanced systemic delivery via co- or sequential administration with permeabilization agents including but not limited to chemical agents, pharmacologic substances (e.g. cytokines), mechanical barrier disruption (e.g. ultrasound, electron paramagnetic resonance (EPR), ultrasound plus microbubbles), and/or osmotic changes (e.g. mannitol), In general the timing and frequency of administration will be adjusted to balance the efficacy of a given treatment or diagnostic schedule with the side-effects of the given delivery system. Exemplary dosing frequencies include, but are not limited to, continuous infusion, single and multiple administrations, hourly, daily, weekly, monthly, or yearly dosing.

Regardless of systemic, intrathecal, or local delivery into the brain parenchyma itself, penetration of bioactive or imaging agents in the brain and other tissues has been a key hurdle to effective therapy and diagnostics. Numerous studies using viral, nanoparticle, and convection-enhanced delivery have failed due to limited movement of substances within the brain. Therefore, defining the critical limiting parameters and designing strategies to enhance brain penetration will likely improve the efficacy of these treatments. Larger nanoparticles offer numerous additional advantages, including increased payload per particle, improved loading efficiency, and prolonged sustained-release kinetics. These factors are known to correlate with the efficacy of many therapeutics and will likely have a significant impact on the utility of nano-sized carriers for diagnostic and therapeutic delivery to the brain.

The composition of the brain ECS, including the physicochemical properties of its components and the space between them ('pores'), are keys factors in the penetration of substances within the brain. Previous efforts to define the ECS pore size have focused on measuring distances between the structures, using electron microscopy, or estimating the spacing based on the spread of various probes within the brain. Early measurements using electron microscopy suggested the upper pore size limit was approximately 20 nm. However, these results were questioned due to tissue fixation and processing artifacts.

More recently, various groups have used fluorescence recovery after photobleaching (FRAP) and integrative optical imaging (IOI) to explore the movements of fluorescent probes within brain slices and the living rat brain. The diffusion limitations of macromolecules (dextrans) and nanoparticles (35 nm PEG-coated quantum dots) in the rat brain in vivo have been investigated. The spread of these fluorescent probes over time were measured using epifluorescence microscopy. From this spread data, the apparent diffusion coefficients were calculated and the ECS width was estimated based on a fluid-filled pore model. They suggested that the rat cortical ECS has pores ranging from 35-60 nm, based on the movement of the 35 nm quantum dot probes. Interpretation of the result was complicated by several factors, including the assumptions of an isotropic, isoporous environment and that the probes used were 'inert' or free from any adhesive interactions. The results obtained were inconsistent due to variable PEG coatings on the 35 nm quantum dots. In addition, convective forces, either CSF bulk flow or those introduced by the injection process, were not accounted for in these calculations. Lastly, while the ECS changes were modeled during terminal ischemia, no attempts were made to control for the metabolic and ECS volume changes known to accompany the administration of anesthetics like urethane. This methodology is limited to assessing probes that diffuse on an experimentally practical time scale and hence, may not be able to assess the movement of larger probes where slow diffusion and no movement are indistinguishable.

The multiple particle tracking (MPT) technique is not limited by these concerns given the high spatial and temporal resolution. MPT has been used to study diffusion limitations in biological media and interfaces, particle characteristics, and intra- and extra-cellular trafficking Using MPT and optimized PEGylation protocols, it has been shown that differences in PEG coating density and molecular weight have a significant impact on shielding particles from adhesive interactions and enabling them to penetrate and distribute more uniformly in vivo.

It has been found unshielded negatively charged particles with exposed hydrophobic polystyrene regions have significantly hindered diffusion regardless of particle size. Often under appreciated, the hydrophobic interactions between particle surfaces and ECS components can be a source of significant adhesion. Adequate surface shielding from potential interactions, including electrostatic and hydrophobic forces, are crucial for rapid diffusion in the brain. Importantly, all surface coatings, including PEG coatings, are not equal. It is particularly difficult to establish dense surface coatings on small particles. It is likely that the PEG-coated quantum dots (35 nm), used in the previous study to set the upper size limit for the brain ECS pores, were not completely shielded, and therefore the transport measurements of this probe were subject to a mixture of electrostatic, hydrophobic, and steric effects.

The present invention will be further understood by reference to the following non-limiting examples.

EXAMPLES

Example 1

Materials and Methods
Brain Tissue Preparation

All experiments were carried out at Johns Hopkins University School of Medicine in accordance with National Institutes of Health guidelines and local Institutional Animal Care and Use Committee regulations. Brain tissue slices were prepared from 130-160 g female Sprague-Dawley rats. Animals were anesthetized with ketamine-xylazine and then administered an intracardiac injection of Euthanosol. After euthanasia, the brain was rapidly removed and immersed in chilled artificial cerebrospinal fluid (ACSF, Harvard Apparatus) supplemented with 10% glucose. Coronal slices were prepared using a rodent brain slice matrix kit (Zivic Instruments, Pittsburgh, Pa.). The matrix and razor blades were washed with 0.9% normal saline and placed on ice prior to inserting the excised rat brain. Placement of the brain and sectioning of the brain was carried out based on instrument instructions such that 1 mm thick slices were obtained. Slices were gently separated with sterile forceps and placed in a Petri dish containing ACSF. Individual slices were then placed in an 8-well glass chamber (Lab-Tek, Campbell, Calif.), and 100 µL of ACSF was added to each well. No liquid was allowed between the tissue and the well bottom in order to prevent interference with imaging and movie acquisition. Using a 10 µL syringe (Hamilton Company, Reno, Nev.) 0.5 µL polystyrene beads were added to the cortical gray matter of the tissue slice. The 8-well chamber was then incubated at 37° C. in a humidity chamber for 30 minutes prior to imaging.

Histochemical Analysis for Tissue Viability

Rat brain slices were analyzed for their glial cytoarchitecture and cell morphology. An intact cytoarchitecture is defined as a tissue slice with a well-preserved (displayed clear astrocyte and neuronal morphology) and uniform composition of glial cells from the surface to the center of the slice. Tissue viability of excised rat brain was tested at time zero, defined as immediately following removal (<2 min.), and time 3 hours, defined as the time at the end point of the imaging and data acquisition. Briefly, the rat brain was excised and slices were prepared as described above. Slices from time 0 and 3 hours were submerged in formaldehyde at room temperature for 24 hours, and then placed in a 70% ethanol solution. Wet tissue slices were then embedded in paraffin and cut into 20 µm thick sections for hematoxylin and eosin staining. The slides were reviewed by a neuropathologist and photographed with a Nikon C1si confocal microscope from the surface to the center of the slice.

Nanoparticle Preparation and Characterization.

Red fluorescent carboxyl modified polystyrene particles 40- to 200-nm in diameter (Molecular Probes, Eugene Oreg.) were covalently modified with methoxy-PEG-amine (molecular weight 5 kDa; Creative PEG Works, Winston-Salem, N.C.) by carboxyl amine reaction, following a modified protocol, as published by Popielarski et al. (2005) *Bioconjug Chem* 16(5):1063-1070, and Suh J, et al. (2007) *Int J Nanomedicine* 2(4):735-741. Briefly, 100 µL of 2% polystyrene particle suspension were washed and resuspended to 4-fold dilution in ultrapure water. An excess of MeO-PEG5000-NH$_2$ was added to the particle suspension in a 1.5 mL Eppendorf tube and mixed to dissolve the PEG. N-hydroxysulfosuccinimide (Sulfo-NHS, Sigma) was added to each tube, and 200 mM borate buffer, pH 8.2, was added up to 1.2 mL total volume. The pH of each reaction tube was adjusted to pH 7.80, and then 1-Ethyl-3-(3-dimethylaminopropyl)carbodiimide (EDC) was added to a concentration of 6.4 mM to each tube. Particle suspensions were placed on a rotary incubator for 4 hours and then glycine (Fisher) was added to quench the reaction. Particle suspensions were then ultracentrifuged (Amicon Ultra 0.5 mL 100 k MW; Millipore, Ireland) to filter and wash any residual reactive compounds. Particles were resuspended in ultrapure water to the original concentration and stored at 4° C. until use.

Size and ζ-potential were determined by dynamic light scattering and laser Doppler anemometry, respectively, using a Zetasizer NanoZS (Malvern Instruments, Southborough Mass.). Size measurements were performed at 25° C. at a scattering angle of 90°. Samples were diluted in 10 mM NaCl, phosphate buffered solution, pH 7.0, and measurements were performed according to instrument instructions. % PEG coating was calculated as previously described by Wang Y Y, et al. (2008) *Angew Chem Int Ed Engl* 47(50): 9726-9729.

Multiple Particle Tracking in Brain Tissue Slices.

Particle transport rates were measured by analyzing trajectories of fluorescent particles that are recorded using a silicon-intensified target camera (VE-1000, Dage MTI, Michine Ind.) mounted on an inverted epifluorescence microscope equipped with a 100× oil-immersion objective (numerical aperture 1.3). Experiments were carried out in 8-well glass chambers (Lab Tek) where diluted particle solutions (0.01% wt/vol) were added to 1 mm thick cortical tissue slices and incubated for 1 h before microscopy. Trajectories of n>100 particles were analyzed for each experiment, and 4 experiments were performed for each condition. Movies were captured with Metamorph software (Universal Imaging, Glendale, Wis.) at a temporal resolution of 66.7 ms for 20 s. The tracking resolution was 10 nm, determined by tracking displacements of particles immobilized with a strong adhesive. The coordinates of nanoparticle centroids were transformed into time-averaged mean square displacement (MSD), $<\Delta r^2(\tau)>=[x(t+\tau)-x(t)]^2+[y(t+\tau)-y(t)]^2$ ($\tau$=time scale or time lag), from which distributions of MSDs and effective diffusivities were calculated, as described by Dawson et al (2003) *J Biol Chem* 278(50): 50393-50401; and Valentine Mont., et al. (2004) *Biophys J* 86(6):4004-4014. The MSD of the nanoparticles vs. $\tau$ can also be fit to the equation MSD=$4D_o\tau^\alpha$ to obtain $\alpha$, the slope of the curve on a log-log scale, which is a measure of the extent of impediment to particle diffusion.

The mechanism of particle transport (diffusive, hindered, or immobile) over short and long time scales was classified based on the concept of relative change (RC) of $D_{eff}$ (Suh, et al. 2007; Suk (2007) *Exp Biol Med (Maywood)* 232(3):461-469). Briefly, RC values of particles at short and long time scales were calculated by dividing the $D_{eff}$ of a particle at a defined time scale by the $D_{eff}$ at an earlier reference time scale. By calculating RC values for two time regimes (i.e. short and long time scales), one can obtain the transport mode that describes the particle transport properties over different length and temporal scales.

Determination of Brain ECS Pore Size

The average pore size of the brain ECS and pore size range was estimated based on fitting an obstruction scaling model to the measured particle diffusion rates using maximum likelihood estimation. C. Nicholson, L. Tao, *Biophys J* 65, 2277 (1993). The model is valid in cases where there is limited interaction between the particles and the ECS components and where fluid in the ECS exhibits micro-viscosity similar to that of water.

Results

Histological Analysis of Rat Brain Cortical Tissue

The brain slice tissue histological patterns did not differ significantly between time 0 hour and 3 hour experimental time points.

Transport of Nanoparticles in Brain ECS

The effect of particle size and surface chemistry determined the transport rates of modified particles in rat brain tissue. The hydrodynamic diameters of the particles are listed in Table 1.

TABLE 1

Physicochemical properties of polystyrene nanoparticles and their diffusivity in normal rat brain tissue ($D_b$) compared to in water ($D_w$)

| Size[a] (nm) | Surface Chemistry | Diameter[b] (nm) | ζ-potential[c] (mV) | % PEG Coating[(31)] | $D_w/D_b^d$ |
|---|---|---|---|---|---|
| 40 | COOH | 54 ± 0.4 | −36 ± 2 | 0 | 76,000 |
| 40 | PEG5k | 61 ± 6 | −0.7 ± 3 | 90 | 9* |
| 100 | COOH | 95 ± 2 | −42 ± 2 | 0 | 16,000 |
| 100 | PEG5k | 108 ± 3 | −2.9 ± 1 | 92 | 60* |
| 200 | COOH | 205 ± 1 | −40 ± 2 | 0 | 48,000 |
| 200 | PEG5k | 242 ± 6 | −5.4 ± 1 | 89 | 2,600* |

The 40 nm, 100 nm, and 200 nm COOH-modified polystyrene particles displayed low transport rates, as measured by geometric ensemble mean squared displacements (<MSD>). At a time scale of 1 s, 40 nm, 100 nm, and 200 nm COOH—PS particles were 76,000-fold, 16,000-fold and 48,000-fold slower in water than the equivalent COOH—PS particles in water.

PEG, a hydrophilic and uncharged polymer, was covalently attached to the surface of 40-, 100-, and 200-nm particles in attempt to reduce electrostatic and hydrophobic interactions with elements in the ECS. The extent of PEG attachment was comparable for all particle sizes as shown by their near-neutral surface charges and % PEG coatings (Table 1).

PEGylation greatly increased particle transport rates for 40- and 100-particles (PEG-PS) as is evident by the 9-fold and 60-fold higher ensemble MSDs ($\tau$=1 s) in water, respectively, compared with corresponding COOH—PS particles of the same size (FIG. 1A-1C). The 200 nm PEG-PS particles showed a lesser increase in particle transport compared to COOH—PS particles of the same size, likely due to significant steric obstruction within the brain ECS. Physical restriction of 200 nm particles compared to 100- and 40-nm PEGylated particles is also supported by representative particle trajectories.

To further evaluate the extent of impediment to particle transport, the $\tau$-dependent {MSD} was fitted to the equation {MSD}=$4D_o\tau^\alpha$, where $D_o$ is the $\tau$-dependent diffusivity and a is the anomalous diffusion exponent that reflects the extent of impediment. An $\alpha$=1 represents unobstructed Brownian diffusion, such as particles in water, where a becomes smaller as obstruction to particle diffusion increases. The $\alpha$ value for 200 nm PEG-PS particles was 0.48, compared to an $\alpha$ value of 0.78 for 100 nm PEG-PS particles. The $\alpha$ value for COOH-modified particles for both 100- and 200-nm PS particles were 0.20 and 0.22, respectively. As expected from the high transport rates of 40 nm PEG-PS particles, the $\alpha$ value was 0.92 compared to an $\alpha$ value of 0.18 for 40 nm COOH—PS particles, further confirming unhindered diffusion of 40 nm well coated particles in brain ECS, slightly hindered diffusion of 100 nm well coated particles, and hindered diffusion of 200 nm well coated particles.

Figures 2A, 2B, 2C:
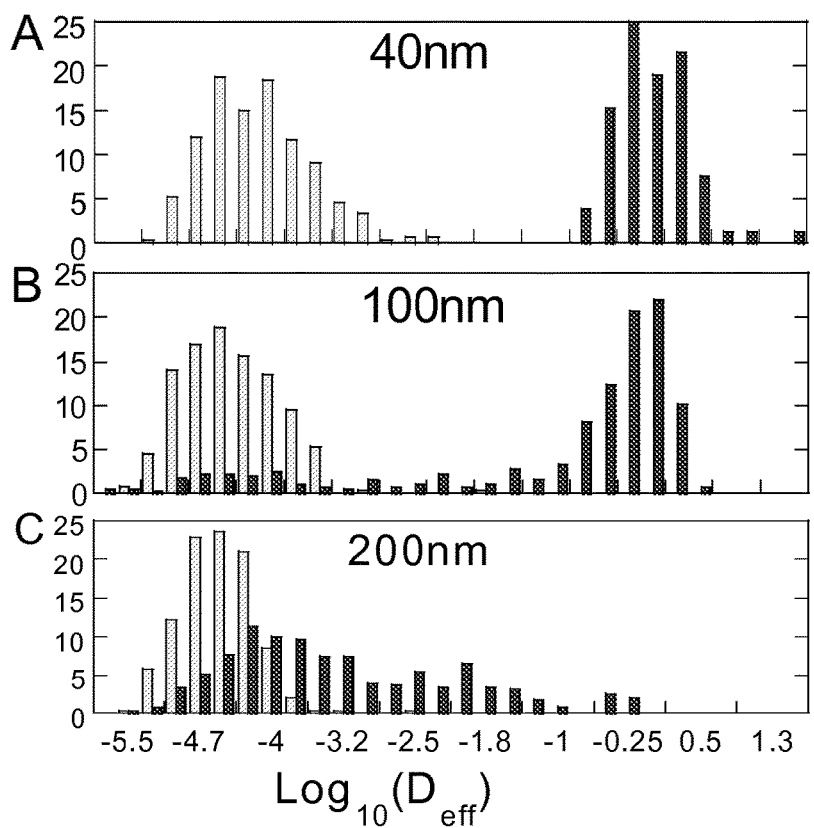
FIGS. 2A (40 nm), 2B (100 nm), and 2C (200 nm) are graphs showing the distribution of the logarithmic $D_{eff}$ of individual nanoparticles (■ PS PEG5k and □ PS COOH) at τ=1 s. Data represents 4 independent experiments, with an average of n>100 nanoparticles per experiment.
Figures 3A, 3B, 3C:
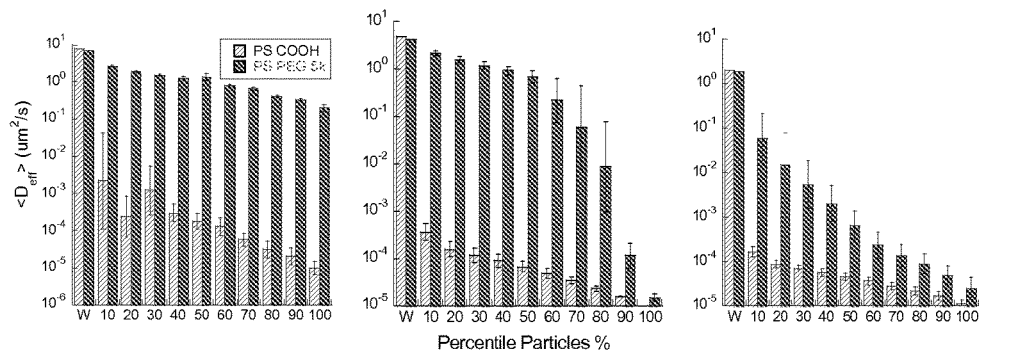
FIGS. 3A, 3B and 3C are graphs showing ensemble-averaged effective diffusivities <$D_{eff}$> of every $10^{th}$ percentile of 40 nm (FIG. 3A), 100 nm (FIG. 3B), and 200 nm (FIG. 3C) COOH—PS (hashed bars) and PEG-PS nanoparticles (solid bars) at τ=1 s, sorted from the fastest 10% of particles ($10^{th}$ percentile) to the slowest 10% of particles ($100^{th}$ percentile). <$D_{eff}$> for the same size particles in water is shown as W. Data represents 4 independent experiments, with average of n>100 particles per experiment.

To ensure that the observed rapid transport of PEGylated nanoparticles was not biased by a small fraction of fast moving outlier particles, the heterogeneity in particle transport rates was evaluated by examining the distribution of individual particle diffusivities at 1 s (FIG. 2). The fastest 75 percent of 40 nm and 65 percent of 100 nm PEG-PS particles exhibited uniformly rapid transport, compared to the fastest 15 percent of 200 nm PEG-PS particles. Fast moving outlier nanoparticles are a subpopulation of interest, as they are more likely to penetrate brain tissue and reach greater distances from the point of injection. Therefore, $D_{eff}$ of individual particles was sorted from fastest to slowest and classified into 10 subgroups (FIG. 3). 40 nm PEG-PS particles showed homogenous distribution, with less than an order of magnitude difference between the fastest and slowest group of particles. The fastest $10^{th}$ percent of 100 nm and 200 nm PEG-PS particles showed 5 and 3 orders of magnitude difference, respectively, from the slowest particles, suggesting that some of the spacing in the ECS could be larger than the predicted 100 nm. However, for all other subgroups (i.e. the slowest 90% of particles) 200 nm PEG-PS particles displayed 2 orders of magnitude lower $D_{eff}$ compared to the same subgroups of 40- and 100-nm PEG-PS particles, leading to an average $D_{eff}$ representative of hindered particle transport.

For all sizes studied, a large fraction of COOH—PS particles appeared to be immobilized or hindered by adhesive interactions with components of the ECS, resulting in an MSD close to the resolution of the microscope. Only a small fraction of COOH—PS particles exhibited Brownian or near-Brownian trajectories for 100- and 200-nm COOH—PS particles, whereas such trajectories were evident for a large fraction of 40- and 100-nm PEG-PS particles.

Figures 4A, 4B:
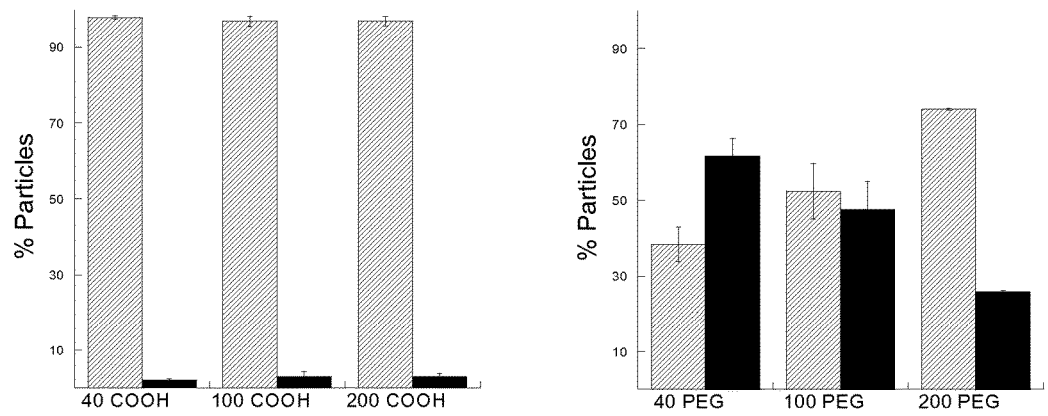
FIGS. 4A and 4B are graphs showing transport mechanism distributions of various sized particles (40 nm, 100 nm, and 200 nm) in normal rat brain tissue with (FIG. 4A) or without (FIG. 4B) PEG coating (n=4 experiments). Data represents mean+/−SEM of 4 experiments, with n>100 particles for each experiment. Immobile particles have an MSD below the microscope detection limit (10 nm). Differences in percentages of immobile+hindered (□), and diffusive particles (■) are statistically significant for 40 nm, 100 nm, 200 nm PEG-PS (FIG. 4B) compared to the COOH-modified particle of the same size (FIG. 4A).

Therefore, to further understand the unexpected rapid transport of 100 nm PEG-PS and to explain the mechanism of the contribution of PEG to improved transport, the percentages of particles undergoing specific modes of transport (diffusive, hindered, or immobile) was determined. The greatly improved transport rates for 40- and 100-nm PS upon PEGylation were largely due to a marked reduction in the number of immobile particles in brain tissue slices. Approximately 60% of well-coated 40- and 45% of 100-nm particles were classified as diffusive, compared to only 2% and 4% of uncoated 40- and 100-nm particles (FIG. 4). PEGylation led to slight improvement in transport of 200 nm PS particles (25% classified as diffusive compared to less than 4% classified as diffusive for uncoated 200 nm PS); however, the majority of particles at this size remained classified as immobile and hindered.

Estimation of Brain ECS Pore Size

Figure 5:
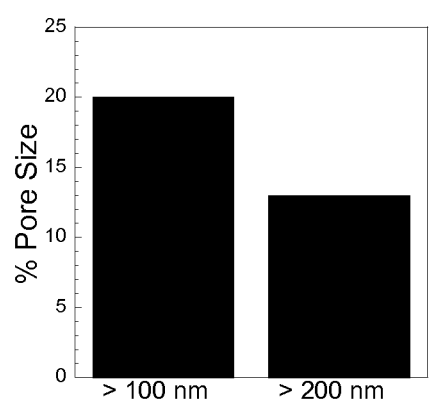
FIG. 5 is a graph showing the percentage of pores larger than 100- and 200-nm. Data represents the ensemble average of four independent experiments with n>100 particles tracked for each experiment.

An effective pore size of the brain ECS can be determined by fitting the measured diffusion rates of 40-, 100-, and 200-nm PEG-PS particles to the obstruction scaling model. Based on the determination that transport was limited due to steric obstruction for larger particles and not due to particle interaction with brain ECS components, diffusion rates for 200 nm PEG-PS particles were incorporated into this model. Using maximum likelihood estimation, the average pore size of normal rat brain ECS was estimated to be between 60-120 nm. The pore size distribution ranged from 20 nm to 230 nm. The largest 20% of pore sizes experienced by particles were >100 nm and 14% of pore sizes experienced by particles were >200 nm (FIG. 5). Overall approximately 60% of the pores sampled by probe particles were larger than 50 nm. The pore size modeling further corroborates the transport rates observed with multiple particle tracking In summary, based on calculations of effective diffusion coefficients for each particle type and size, non-adhesive particles as large as 110 nm should diffuse rapidly in brain ECS.

The results show the transport of negative, hydrophobic polystyrene particles without adequate PEG coatings was characterized by significant entrapment within and adhesion to the brain extracellular network. This can likely be attributed to the hydrophobic carboxylate polystyrene beads forming polyvalent bonds with hydrophobic and/or charged domains or components of the brain ECS.

It should be noted that 40 nm COOH—PS particles showed an even larger difference in diffusion in brain ECS versus water ($D_b/D_w=76,000$) compared to 100 nm and 200 nm COOH—PS. 40 nm COOH—PS particles were more frequently localized within cells or small micro-domains compared to larger particles, thereby explaining the more restricted diffusivity of this particle type. Regardless of size, the strongly hindered movements of COOH-modified particles suggest that hydrophobic interactions between the particle surface and elements of brain ECS also play an important role in limiting particle diffusion throughout the brain tissue.

Rapid transport of particles in biological mediums requires surfaces that are densely coated, creating a hydrophilic and net-neutral shell that minimizes hydrophobic and electrostatic adhesive interactions. However, the engineering of densely charged yet neutral surfaces on synthetic particles is not straightforward. The effectiveness of the PEG shield was determined to be consistent for all particle sizes used in this study, as measured by surface charge and resistance to small molecule absorption. These densely coated 40 nm and 100 nm PEG-PS nanoparticles led to a greatly increased percentage of diffusive particles and up to 5 and 3 orders of magnitude, respectively, of faster transport. It is apparent that 200 nm PEG-PS nanoparticles, while showing a slight increase in particle transport compared to COOH-modified particles, are on average too large to diffuse rapidly through brain ECS. The small percentage of 200 nm PEG-PS particles that are classified as diffusive suggests that there are some pores in brain ECS large enough to accommodate larger particles. The demonstration that 20% of the pores analyzed were greater than 100 nm and 14% were greater than 200 nm indicates that a significant percentage of well-coated particles up to 110 nm, and some well-coated particles up to 230 nm, can diffuse by accessing larger pores found throughout the brain ECS.

While this study utilized an ex vivo model, which may be affected by the tissue removal and preparation process, histological inspection revealed apparent recovery from ischemic morphologies and good preservation of tissue architecture. Even without this apparent recovery, the findings here would theoretically underestimate the ECS mesh size given the changes described during terminal ischemia. Importantly, observations in this model would not be influenced by the bulk flow phenomenon inherent to the living system. Yet, regardless of this difference, the multiple particle tracking technique and analysis used here is designed to eliminate particles showing convective or bulk flow movements.

Example 2: Determination of Size and Effect of Charge on Transport of Nanoparticles Through Brain Tissue Materials and Methods Nanoparticle Preparation and Characterization Forty- to 200-nm red fluorescent carboxyl modified polystyrene particles (Molecular Probes, Eugene Oreg.) were covalently modified with methoxy-PEG-amine (molecular mass 5 kDa; Creative PEG Works, Winston-Salem, N.C.) by carboxyl amine reaction. Briefly, 100 µL of 2% polystyrene particle suspension were washed and resuspended to 4-fold dilution in ultrapure water. An excess of MeO-PEG5000-NH2 was added to the particle suspension in a 1.5 mL Eppendorf tube and mixed to dissolve the PEG. Sulfo-NHS (Sigma) was added to each tube, and 200 mM borate buffer, pH 8.2, was added to a 4-fold dilution of the starting volume. The pH of each reaction tube was adjusted to pH 7.80, and then EDC was added to a concentration of 6.4 mM to each tube. Particle suspensions were placed on a rotary incubator for 4 hours and then ultracentrifuged (Amicon Ultra 0.5 mL 100 k MWCO; Millipore, Ireland) to filter and wash any residual reactive compounds. Particles were resuspended in ultrapure water to the original concentration and stored at 4° C. until use.

Size and $\zeta$-potential were determined by dynamic light scattering and laser Doppler anemometry, respectively, using a Zetasizer NanoZS (Malvern Instruments, Southborough Mass.). Size measurements were performed at 25° C. at a scattering angle of 90°. Samples were diluted in 10 mM NaCl, phosphate buffered solution, pH 7.0, and measurements were performed according to instrument instructions. Percent PEG coating was calculated as described by Y. Y. Wang et al., *Angew Chem Int Ed Engl* 47, 9726 (2008).

Neocortical Slice Preparation

Each component of this study was approved by the Institutional Review Board. Neocortical slices were prepared from tissue obtained in the operating room during epilepsy surgery. Following removal from the patient, the tissue was rapidly divided into the components needed for pathological analysis; the remaining tissue was placed in normal saline on ice and transported immediately to the laboratory for slice preparation. The tissue was immersed in chilled artificial cerebrospinal fluid (ACSF, Harvard Apparatus) supplemented with 10 mM glucose. Coronal slices were prepared using a rodent brain slice matrix kit (Zivic Instruments, Pittsburgh, Pa.). The matrix and razor blades were washed with 0.9% normal saline, and placed on ice prior to inserting the excised rat brain. This chilled preparation process served two key purposes: (1) protect the tissue from ischemia-mediated damage and swelling, and (2) enable accurate cutting of fresh, gelatinous tissue.

Placement of the brain and sectioning of the brain was carried out based on instrument instructions so that 1 mm thick slices were obtained. Slices were gently separated with sterile forceps and placed in a Petri dish containing ACSF. Individual slices were then placed in an 8-well glass chamber (Lab-Tek, Campbell, Calif.) and 200 µL of ACSF was added to each well, with no liquid between the tissue-well bottom interface. Liquid between the interface was found to interfere with imaging and movie capture. Using a 10 µL syringe (Hamilton Company, Reno, Nev.), 0.5 µL polystyrene beads were added to the gray matter region 500 um into the 1 mm thick tissue. The 8-well chamber was then incubated at 37° C. in humidity chamber for 30 minutes prior to imaging to allow tissue recovery and convection dissipation.

Multiple Particle Tracking in Neocortical Slices

Particle transport rates were measured by analyzing trajectories of fluorescent particles, recorded by using a silicon-intensified target camera (VE-1000, Dage MTI, Michine Ind.) mounted on an inverted epifluorescence microscope equipped with a 100× oil-immersion objective (numerical aperture 1.3). Trajectories of at least 100 particles per sample and particle type were analyzed. Five separate brain tissue specimens were used for each particle type. Movies were captured using Metamorph software (Universal Imaging, Glendale, Wis.) at a temporal resolution of 66.7 frames per milliseconds over 20 seconds. Based on the tracking displacements of particles immobilized with a strong adhesive, this experimental setup resulted in a tracking resolution of 10 nanometers. The coordinates of nanoparticle centroids were transformed into time-averaged MSD, based on equation 1:

$$<\Delta r^2(\tau)>=[x(t+\tau)-x(t)]^2+[y(t+\tau)-y(t)]^2 \quad (1)$$

($\tau$=time scale or time lag)

Distributions of MSDs and effective diffusivities were calculated, as previously demonstrated. (92) The MSD of the nanoparticles vs. $\tau$ can also be fit to the equation 2:

$$MSD=4D_o\tau^\alpha \quad (2)$$

Based on this relationship, the slope of the MSD versus time curve on a log-log scale, is given by a, which represents a measure of the extent of impediment to particle diffusion (Suh, et al., *Adv Drug Deliv Rev* 57, 63 (2005)).

Particle Transport Mode Classification

The mechanism of particle transport over short and long time scales was classified based on the concept of relative change (RC) of effective diffusion ($D_{eff}$). RC values of particles at varying time scales were calculated by dividing the $D_{eff}$ of a particle at a known time scale by the $D_{eff}$ at an earlier reference time scale. By calculating RC values for two time regimes (i.e., short and long time scales), one can obtain the transport mode that describes the particle transport properties over different distance and temporal scales. The short relative change interval ($RC_{short}$) was defined at $\tau_{ref}$=0.2 s, and $\tau_{probe}$=1 s, whereas the long relative change interval ($RC_{long}$) was found at reference $\tau_{ref}$=1 s and $\tau_{probe}$=2 s. The accuracy of the transport-mode classification was confirmed by the slopes of the MSD versus time plots, where diffusive particles generated slope values of ~1[UNITS] and more hindered particles gave progressively lower values with increasing time scale.

Histo-Pathological Analysis of Human Brain Slices

The human brain tissue slices were studied using standard hematoxylin and eosin (H&E) based techniques to identify changes in histological architecture and cell morphology introduced by the preparation and incubation process. Representative tissue slices were preserved in formalin immediately following sectioning in the laboratory and after completing data acquisition, approximately 3 hours following removal, preparation, incubation, and particle imaging. The tissue was removed from the formalin after 24 hours and placed in 70% ethanol solution until paraffin embedding, sectioning, and H&E staining. The tissue sections were reviewed with a senior neuropathologist for evidence of tissue changes and damage.

In Vivo Mouse Brain Imaging of Nanoparticle Spread

All aspects of these experiments were approved by the institutional Animal Care and Use Committee. To create a stable, immobile cranial window, a warm agarose solution (20% weight/volume) was placed over the exposed brain region and a 5 mm glass coverslip was quickly placed prior to agarose cooling and gelatinization. A custom circular metal bar was secured to the adjacent bone just lateral to the sagittal suture on the right side using a small drop of fast-drying adhesive. Cement (HyBond, Inc.) was then applied to secure the agarose, glass, and metal bar construct rigidly to the calvarium. A channel representing approximately 90 degrees of the cover glass circle was not cemented and left exposed for the glass pipette to insert into the brain.

The cranial bar was secured to a custom microscope stage allowing stable imaging of the anesthetized mouse. A 20× microscope objective (Zeiss Inc., Plan-Apochromat [numerical aperture: 1.0, working distance 1.9 mm]) was used for imaging and images were collected using a photomultiplier non-descanned detector. The micro-injection apparatus attached to a stereotactic manipulator (Drummond Scientific Inc.) was fixed with a glass micropipette (tip diameter approximately 30 µm), loaded with nanoparticle solution, and positioned for injection through the agarose channel into the brain. A blood vessel-free region of cortex was identified, and the micropipette was gently inserted to a depth of 100-200 um below the pial surface under direct visualization, and withdrawn slightly to create a small pocket to receive the injection. The nano-injection device was set to inject 9.2 nanoliters at the 'slow' setting. Particle combinations were injected at approximately equivalent concentrations and data were captured every 5 minutes for 30 minutes.

Results

Human Brain ECS Pores are Larger than Previously Reported.

Fluorescent particles with extremely dense PEG coatings were added to fresh human brain cortex immediately following removal from patients undergoing epilepsy surgery. The particle Brownian motions were then quantified using ex vivo high-resolution multiple-particle tracking (MPT). The results are shown in Table 2.

TABLE 2

Physicochemical properties of polystyrene nanoparticles and their diffusivity in human cortical tissue ($D_b$) compared to in water ($D_w$)

| Size[a] (nm) | Surface Chemistry | Diameter[b] (nm) | ζ-potential[c] (mV) | % PEG Coating[(31)] | $D_w/D_b$[d] |
|---|---|---|---|---|---|
| 40 | Methoxy-PEG 5k | 56 ± 4 | −1.7 ± 2 | 90 | 60* |
| 40 | COOH | 43 ± 0.7 | −41 ± 2 | | 110,000 |
| 100 | Methoxy-PEG 5k | 105 ± 1 | −3.9 ± 0.5 | 93 | 50* |
| 100 | COOH | 92 ± 2 | −44 ± 2 | | 55,000 |
| 200 | Methoxy-PEG 5k | 230 ± 5 | −7.3 ± 2 | 91 | 9000* |
| 200 | COOH | 210 ± 1 | −45 ± 2 | | 150,000 |

[a]Provided by manufacturer
[b]Measured by dynamic light scattering. Error values represent standard error of the mean.
[c]Measure at pH 7.0. Error values represent standard error of the mean.
[d]Effective diffusivity in brain tissue is calculated at time scale of 1 s and nanoparticle diffusivity in water is calculated from Stokes-Einstein equation using average particle diameter.
*Statistically significant compared to COOH modified particle of similar size The 40 nm and 100 nm PEG-coated particles exhibited ensemble geometric mean square displacements (MSD) that were 2000- and 1000-fold higher than similar sized uncoated particles, respectively (Table 2).

Surprisingly, these particles diffused only 50 times slower in the human brain than in pure water. Therefore, the dense PEG coatings allowed 40 nm and 100 nm particles to experience the brain ECS as a visco-elastic liquid rather than a visco-elastic solid. In contrast, the 200 nm PEG-coated particles were 9000-times slower in the brain than in water and 100-fold slower than the 100 nm PEG-coated particles in the brain. Representative particle trajectories for PEG-coated and uncoated 40 nm, 100 nm, and 200 nm particles are provided in FIG. 1A-C.

Uncoated particles exhibited highly constrained motion regardless of size, whereas the same particles densely coated with PEG exhibited diffusive motion for 40 nm and 100 nm particles, but hindered motion for 200 nm. To determine the effective pore size range in the brain ECS, the Amsden obstruction scaling model for entangled and cross-linked gels was fit to the MSD data. The human tissue ECS was found to have pores as large as 300 nm, with 21% of pores greater than 100 nm and 9% greater than 200 nm (FIG. 5A). The smallest pores experienced by the probe particles were <40 nm, similar to previous reports based on electron microscopy and Fick's Law-based diffusion analysis of poorly coated nanoparticles.

For all sizes studied, the majority of uncoated particles (COOH—PS) were immobilized within the extracellular space, resulting in mean square displacements below the resolution of the microscope. The remainder of the COOH—PS particles exhibited hindered diffusive motions. Together these observations suggest that regardless of particle size, adhesive interactions, electrostatic [negatively-charged carboxylate surface] and hydrophobic [exposed polystyrene surfaces], significantly limit particle diffusion within the brain.

Nanoparticle Tracking in Live Mouse Brain Confirms the Larger ECS Pore Size.

Using live-animal brain imaging in mice, nanoparticle penetration in vivo was detected. Red-fluorescent, uncoated (COOH—PS) and green-fluorescent coated (PEG-PS) particles with similar diameters were co-injected into the living mouse cerebral cortex at a depth of 100-200 microns below the pial surface. Real time video microscopy showed that uncoated particles were uniformly stuck in the tissue while 40 nm and 100 nm particles with dense PEG coatings penetrated into the tissue over the 30 minute imaging interval. Representative, non-convective particle trajectories from separate regions within the brain showed much greater MSD for the 100 nm PEG-coated particles compared to the PEG-coated 200 nm and uncoated 100 nm and 200 nm particles. The individual movements of 40 nm particles in vivo could not be resolved due to the fast movement of particles and temporal and spatial resolution limitations of a laser scanning microscope. To confirm these differences further, co-injections of the PEG-coated red and green fluorescent particles of different sizes were performed. Similar to the human brain ex vivo, the 40 nm and 100 nm PEG-coated particles rapidly penetrated the mouse brain, whereas the 200 nm PEG-coated particles penetrated to a considerably lower extent, confirming relatively few ECS pores ≥200 nm.

Representative hematoxylin and eosin sections of the initial and post-acquisition human brain tissue did not show significant differences between these two time points suggesting minimal tissue damage introduced by tissue removal, collection, and processing. The lack of cellular swelling, picnotic nuclei, or ischemic morphologies was observed.

Uncoated and PEG-coated fluorescent, carboxyl-modified polystyrene particles sized 40 nm, 100 nm, and 200 nm were measured by laser Doppler anemometry for net surface charge (ξ-potential) and hydrodynamic diameter. Example 1 showed that the transport of particles through biological media is critically dependent on the type and density of PEG on the particle surface. This discovery enabled the preparation of non-adhesive particles for this study. The PEG-coated particles were 10-20 nm larger than the unmodified particles and had a near neutral net surface charge.

In this study, ex vivo and in vivo multiple particle tracking was used to analyze the non-convective movements of densely coated nanoparticles of various sizes in the human brain. These particles were also directly injected into the cerebral cortex of living mice, confirming the characteristics of brain penetrating nanoparticles in vivo. Importantly, the results from these two models aligned closely, producing the surprising results that: (1) the brain ECS has a large percentage of pores >100 nm, and (2) particles larger than the reported ECS mesh size (≤40 nm) rapidly penetrate within the brain, but only if well-coated to minimize adhesive interactions.

We claim:

1. A dosage formulation for delivery of a therapeutic, prophylactic or diagnostic agent to the brain, the formulation consisting of
   a. polymeric nanoparticles having a diameter of at least about 40 nm and less than about 200 nm, the nanoparticles having a hydrophobic polymeric core and being coated with a hydrophilic polymer comprising polyalkylene oxide or a block copolymer containing polyalkylene oxide blocks, in an amount effective to result in a neutral or near neutral charged surface between −10 mV and 10 mV measured as zeta-potential in phosphate buffered solution, pH 7.0 using laser Doppler anemometry and having a number density of at least 0.1 hydrophilic polymer per $nm^2$ of nanoparticle surface, wherein the hydrophilic polymer is present in a weight percent of greater than 80% relative to the total weight of the polymeric nanoparticles,
   b. an effective amount of a therapeutic, prophylactic or diagnostic agent to prevent or treat a disease or disorder of the brain, encapsulated in or on the nanoparticles, and
   c. a pharmaceutically acceptable excipient for delivery into the brain,
   wherein the nanoparticles have a diffusion rate at most about 60-fold slower in the brain than in water, whereas the same nanoparticles without the hydrophilic polymer coating have a diffusion rate at least about 16,000-fold slower in the brain than in water, characterized by measuring average effective diffusivities at a time scale of 1 second of respective nanoparticles in cortical tissue relative to in water ($D_w/D_b$).

2. The formulation of claim 1 wherein the nanoparticles are coated with polyethylene glycol or a block copolymer containing polyethylene glycol blocks.

3. The formulation of claim 1, wherein the hydrophilic polymer has a number density of at least 0.2, 0.5, 1, 2, 5, 10, 15, 20, 25, 40, 50, 60, 75, 90, or 100 hydrophilic polymer per $nm^2$ of nanoparticle surface.

4. The formulation of claim 1, wherein the hydrophilic polymer has a mass of at least 9/10 of the mass of the nanoparticles.

5. The formulation of claim 1, wherein the hydrophilic polymer has a weight percent of at least 81%, 82%, 83%, 84%, 85%, 86%, 87%, 88%, 89%, 90%, 91%, 92%, 93%, 94%, 95%, or greater relative to the total weight of the polymeric nanoparticles.

6. The formulation of claim 1, wherein the nanoparticles are formulated for direct injection into the brain.

7. The formulation of claim 1, wherein the polymeric core is formed of a biocompatible biodegradable polymer.

8. The formulation of claim 1, wherein the nanoparticles have an average diameter of about 110 nm, 120 nm, 130 nm, 140 nm, 150 nm, 160 nm, 170 nm, 180 nm, or 190 nm.

9. The formulation of claim 1, wherein the therapeutic, prophylactic or diagnostic agent is loaded at a weight percent of between about 1% and about 80%, between about 1% and about 50%, between about 1% and about 40%, between about 1% and about 20%, or between about 1% and about 10%, relative to the total weight of the nanoparticles and the therapeutic, prophylactic or diagnostic agent.

10. The formulation of claim 1 in the form of a nanoparticle suspension in an aqueous medium, wherein, following administration, the nanoparticles release an effective amount of the therapeutic, prophylactic or diagnostic agent in the brain over a period of at least 10 minutes, 20 minutes, 30 minutes, one hour, two hours, four hours, six hours, ten hours, one day, three days, seven days, ten days, two weeks, one month, or longer.

11. A method for treating a disease or disorder of the brain, the method comprising administering to the brain the formulation of claim 1.

12. The method of claim 11, wherein the formulation is administered directly to the brain.

13. The method of claim 11, wherein the formulation is administered systemically and the nanoparticles penetrate the brain by passing through the blood-brain barrier.

14. The method of claim 13, wherein the formulation is administered in combination with one or more techniques to facilitate passage of the nanoparticles through the blood brain barrier.

15. The method of claim 14, wherein the technique is selected from the group consisting of electron paramagnetic resonance, ultrasound, and ultrasound plus microbubbles.

16. The method of claim 11, wherein the disease or disorder is selected from the group consisting of tumors, neurological disorders, and brain injury or trauma.

17. The dosage formulation of claim 1, wherein the nanoparticles have an average diameter between about 60 and about 110 nm.

18. The dosage formulation of claim 1, wherein the nanoparticles have an average diameter of at least 110 nm and less than 200 nm.

19. The formulation of claim 9, wherein the therapeutic, prophylactic or diagnostic agent is loaded at a weight percent between about 1% and about 40% relative to the total weight of the nanoparticles and the therapeutic, prophylactic or diagnostic agent.

20. The formulation of claim 9, wherein the therapeutic, prophylactic or diagnostic agent is loaded at a weight percent between about 1% and about 10% relative to the total weight of the nanoparticles and the therapeutic, prophylactic or diagnostic agent.

* * * * *